(12) United States Patent
Chen et al.

(10) Patent No.: US 8,968,703 B2
(45) Date of Patent: Mar. 3, 2015

(54) $^{13}$C-MR DETECTION USING HYPERPOLARISED $^{13}$C-FRUCTOSE

(75) Inventors: Albert Chen, Toronto (CA); David Wilson, San Francisco, CA (US); John Kurhanewicz, South San Francisco, CA (US); Daniel Blackburn Vigneron, Corte Madera, CA (US); Kayvan Keshari, Stockton, CA (US)

(73) Assignees: GE Healthcare Limited, Buckinghamshire (GB); The Regents of the University of California, Oakland, CA (US)

( * ) Notice: Subject to any disclaimer, the term of this patent is extended or adjusted under 35 U.S.C. 154(b) by 22 days.

(21) Appl. No.: 13/395,182

(22) PCT Filed: Sep. 8, 2010

(86) PCT No.: PCT/EP2010/063194
§ 371 (c)(1),
(2), (4) Date: Jun. 18, 2012

(87) PCT Pub. No.: WO2011/029854
PCT Pub. Date: Mar. 17, 2011

(65) Prior Publication Data
US 2012/0258050 A1   Oct. 11, 2012

(30) Foreign Application Priority Data
Sep. 10, 2009 (EP) .................... 09169919

(51) Int. Cl.
*A61B 5/055* (2006.01)
*A61K 49/04* (2006.01)
*G01R 33/56* (2006.01)
*A61K 49/10* (2006.01)
*G01N 24/08* (2006.01)
*G01R 33/46* (2006.01)
*G01R 33/485* (2006.01)
*G01R 33/62* (2006.01)

(52) U.S. Cl.
CPC ............ *G01R 33/5601* (2013.01); *A61B 5/055* (2013.01); *A61K 49/10* (2013.01); *G01N 24/088* (2013.01); *G01R 33/46* (2013.01); *G01R 33/485* (2013.01); *G01R 33/5605* (2013.01); *G01R 33/62* (2013.01)
USPC ............................................ 424/9.3; 424/9.4

(58) Field of Classification Search
USPC .................................................... 424/9.3, 9.4
See application file for complete search history.

(56) References Cited

U.S. PATENT DOCUMENTS

2004/0039281 A1   2/2004   Cook et al.
2008/0260649 A1   10/2008  Thaning et al.

FOREIGN PATENT DOCUMENTS

| WO | WO9839277 A1 * | 9/1998 |
| WO | 9935508 A1 | 7/1999 |
| WO | 2008020765 A2 | 2/2008 |

OTHER PUBLICATIONS

PCT Search Report Issued in International Application PCT/EP2010/063194 Date of Search Report Jan. 21, 2011 (11 Pages).
Keshari Kayvan R. et al: "Hyperpolarized [2-C-13]-Fructose: A Hemiketal DNP Substrate for In Vivo Metabolic Imaging", Journal of the America Chemical Society, vol. 131, No. 48, Dec. 2009 pp. 17591-17596, XP002616020, ISSN 0002-7863.

* cited by examiner

*Primary Examiner* — Benjamin Packard

(57) ABSTRACT

The invention relates to a method of $^{13}$C-MR detection using an imaging medium comprising hyperpolarised $^{13}$C-fructose and to an imaging medium containing hyperpolarised $^{13}$C-fructose for use in said method.

11 Claims, 3 Drawing Sheets

¹³C-MR DETECTION USING HYPERPOLARISED ¹³C-FRUCTOSE

CROSS-REFERENCE TO RELATED APPLICATIONS

This application is a filing under 35 USC 371 and claims priority to international patent application number PCT/EP2010/063194 filed on 8 Sep. 2010, published on 17 Mar. 2011 as WO-2011/029854-A1, which claims priority to European Patent Application EP09169919.9 filed in EP on 10 Sep. 2009.

FIELD

The invention relates to a method of $^{13}$C-MR detection using an imaging medium comprising hyperpolarised $^{13}$C-fructose and to an imaging medium containing hyperpolarised $^{13}$C-fructose for use in said method.

BACKGROUND OF THE INVENTION

Magnetic resonance (MR) imaging (MRI) is a technique that has become particularly attractive to physicians as images of a patients body or parts thereof can be obtained in a non-invasive way and without exposing the patient and the medical personnel to potentially harmful radiation such as X-rays. Because of its high quality images and good spatial and temporal resolution, MRI is a favourable imaging technique for imaging soft tissue and organs.

MRI may be carried out with or without MR contrast agents. However, contrast-enhanced MRI usually enables the detection of much smaller tissue changes which makes it a powerful tool for the detection of early stage tissue changes like for instance small tumours or metastases.

Several types of contrast agents have been used in MRI. Water-soluble paramagnetic metal chelates, for instance gadolinium chelates like Omniscan™ (GE Healthcare) are widely used MR contrast agents. Because of their low molecular weight they rapidly distribute into the extracellular space (i.e. the blood and the interstitium) when administered into the vasculature. They are also cleared relatively rapidly from the body.

Blood pool MR contrast agents on the other hand, for instance superparamagnetic iron oxide particles, are retained within the vasculature for a prolonged time. They have proven to be extremely useful to enhance contrast in the liver but also to detect capillary permeability abnormalities, e.g. "leaky" capillary walls in tumours which are a result of tumour angiogenesis.

WO-A-99/35508 discloses a method of MR investigation of a patient using a hyperpolarised solution of a high $T_1$ agent as MRI contrast agent. The term "hyperpolarisation" means enhancing the nuclear polarisation of NMR active nuclei present in the high $T_1$ agent, i.e. nuclei with non-zero nuclear spin, preferably $^{13}$C- or $^{15}$N-nuclei. Upon enhancing the nuclear polarisation of NMR active nuclei, the population difference between excited and ground nuclear spin states of these nuclei is significantly increased and thereby the MR signal intensity is amplified by a factor of hundred and more. When using a hyperpolarised $^{13}$C- and/or $^{15}$N-enriched high $T_1$ agent, there will be essentially no interference from background signals as the natural abundance of $^{13}$C and/or $^{15}$N is negligible and thus the image contrast will be advantageously high. The main difference between conventional MRI contrast agents and these hyperpolarised high $T_1$ agents is that in the former changes in contrast are caused by affecting the relaxation times of water protons in the body whereas the latter class of agents can be regarded as non-radioactive tracers, as the signal obtained arises solely from the agent.

A variety of possible high $T_1$ agents for use as MR imaging agents are disclosed in WO-A-99/35508, including non-endogenous and endogenous compounds. As examples of the latter intermediates in normal metabolic cycles are mentioned which are said to be preferred for imaging metabolic activity. By in vivo imaging of metabolic activity, information of the metabolic status of a tissue may be obtained and said information may for instance be used to discriminate between healthy and diseased tissue.

Pyruvate for instance is a compound that plays a role in the citric acid cycle and the conversion of hyperpolarised $^{13}$C-pyruvate to its metabolites hyperpolarised $^{13}$C-lactate, hyperpolarised $^{13}$C-bicarbonate and hyperpolarised $^{13}$C-alanine can be used for in vivo MR studying of metabolic processes in the human body. Hyperpolarised $^{13}$C-pyruvate may for instance be used as an MR imaging agent for in vivo tumour imaging as described in detail in WO-A-2006/011810 and for assessing the viability of myocardial tissue by MR imaging as described in detail in WO-A-2006/054903.

The metabolic conversion of hyperpolarised $^{13}$C-pyruvate to its metabolites hyperpolarised $^{13}$C-lactate, hyperpolarised $^{13}$C-bicarbonate and hyperpolarised $^{13}$C-alanine can be used for in vivo MR study of metabolic processes in the human body since said conversion has been found to be fast enough to allow signal detection from the parent compound, i.e. hyperpolarised $^{13}$C$_1$-pyruvate, and its metabolites. The amount of alanine, bicarbonate and lactate is dependent on the metabolic status of the tissue under investigation. The MR signal intensity of hyperpolarised $^{13}$C-lactate, hyperpolarised $^{13}$C-bicarbonate and hyperpolarised $^{13}$C-alanine is related to the amount of these compounds and the degree of polarisation left at the time of detection, hence by monitoring the conversion of hyperpolarised $^{13}$C-pyruvate to hyperpolarised $^{13}$C-lactate, hyperpolarised $^{13}$C-bicarbonate and hyperpolarised $^{13}$C-alanine it is possible to study metabolic processes in vivo in the human or non-human animal body by using non-invasive MR imaging or MR spectroscopy. Due to the limited lifetime of the hyperpolarised nucleus, with signal decay dependant on $T_1$ relaxation, carboxylated carbons have been the primary targets for development of imaging agents for studying of metabolic processes. Carbonyl carbons, which lack attached protons and limit the relaxation as a result of dipolar cross relaxation, have been the standard species to table and polarize with $T_1$'s on the order of 40-60 seconds, depending on the field strength. However, the use of imaging agents which are isotopically enriched and hyperpolarised at carbonyl carbons makes it difficult to investigate upstream glycolytic processes, which have been related to both cancer metabolism as well as other metabolic abnormalities, such as fatty liver disease and diabetes. Although a number of molecules of interest have been polarized and observed through their carbonyl carbones, a great number of important metabolic intermediates do not contain a carbonyl. Hence imaging agents providing complimentary metabolic information have been sought.

SUMMARY OF THE INVENTION

It has now surprisingly identified been that hyperpolarised $^{13}$C-fructose may be used as an imaging agent.

Fructose, occurring as an isomeric mixture of five and six membered rings, has as its most stable isomer β-fructopyranose with hemiketal in the C2 position. Fructose can enter glycolysis via hexokinase or fructokinase. The one-step metabolism via hexokinase to the phosphorylated fructose-6-phosphate is analogous to the first step of glycolysis, in which glucose is phosphorylated to glycose-6-phosphate. The metabolic flux to fructose-6-phosphate in the cell is related to the downstream glycolytic metabolic events as well as activity of the pentose phosphate pathway (PPP). The PPP is responsible for the predominant amount of nucleotide synthesis, which is increased at high turnover rates, and has been postulated to be the source of regeneration of NADPH in cancer cells making them more resistant to oxidative stress and allowing them to replenish glutathione. Furthermore, metabolism of fructose is implicated in non-alcoholic steatohepatitis (NASH), and in the pathogenesis of specific types of cancer. Fructose can also be metabolized to the fructose-1-phosphate via fructokinase, a reaction that takes place primarily in the liver. Hepatic uptake is via the GLUT5 transporter that demonstrates relative specificity for fructose. Expression of this transporter may be an important biomarker for disease in extrahepatic tissues. For example, the human fructose transpoter, GLUT5 is highly expressed in breast cancer cell lines but not by normal breast tissue. A relationship between fructose and benign cancer tissue in prostate gland has also been shown. Thus, by using hyperpolarised $^{13}$C-fructose as an imaging agent, metabolic activity can be assessed, and as there are different uptake mechanisms for fructose than for known hyperpolarized $^{13}$C-MR imaging agents, such as for $^{13}$C pyruvate, additional metabolic information may be obtained and new applications are enabled.

Thus, in a first aspect the invention provides a method of $^{13}$C-MR detection using an imaging medium comprising hyperpolarised $^{13}$C-fructose.

Yet another aspect of the invention is a composition comprising hyperpolarised sodium $^{13}$C-fructose, optionally a trityl radical and optionally a paramagnetic metal ion, wherein said composition is obtained by dynamic nuclear polarisation. When preparing the composition comprising hyperpolarised sodium $^{13}$C-fructose the trityl radical used a DNP agent may optionally be removed as a final step.

Yet another aspect of the invention is hyperpolarized $^{13}$C-fructose, preferably [2-$^{13}$C]-fructose.

Yet another aspect of the invention is an imaging medium comprising hyperpolarized $^{13}$C-fructose, preferably [2-$^{13}$C]-fructose. The imaging medium according to the invention may be used as imaging medium in $^{13}$C-MR detection.

DETAILED DESCRIPTION OF THE EMBODIMENTS

Figure 1:
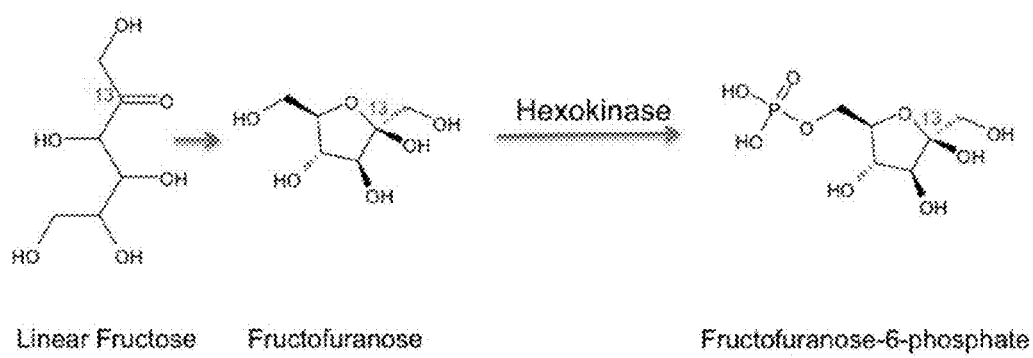
FIG. 1. The mechanism for transport by GLUT5 and the first step of metabolism of fructose to fructofuranose-6-phosphate by hexokinase.

The term "imaging medium" denotes a liquid composition comprising hyperpolarised $^{13}$C-fructose as the MR active agent, i.e. imaging agent. The imaging medium according to the invention may be used as imaging medium in a method of $^{13}$C-MR detection. Hence, another aspect of the invention is an imaging medium comprising hyperpolarised $^{13}$C-fructose for use in a method of $^{13}$C-MR detection.

The imaging medium used in the method of the invention may be used as an imaging medium for in vivo $^{13}$C-MR detection, i.e. in living human or non-human animal beings. Further, the imaging medium used in the method of the invention may be used as imaging medium for in vitro $^{13}$C-MR detection, e.g. in cell cultures, body samples like for instance urine, saliva or blood, ex vivo tissue, for instance ex vivo tissue obtained from a biopsy or isolated organs.

The term "$^{13}$C-MR detection" denotes $^{13}$C-MR imaging or $^{13}$C-MR spectroscopy or combined $^{13}$C-MR imaging and $^{13}$C-MR spectroscopy, i.e. $^{13}$C-MR spectroscopic imaging. The term further denotes $^{13}$C-MR spectroscopic imaging at various time points.

Fructose, with molecular formula $C_6H_{12}O_6$, is also called D-arabino-hexulose, fruit sugar, beta-levulose and Levulose. Fructose is a very sweet sugar occurring in many fruits, vegetables and honey and is used as a preservative for foodstuff and as an intravenous nutrient. Fructose is a monosaccharide with a ketone functional group. Fructose is an isomer of glucose. When dissolved in solution, it forms ring structures similar to glucose, which are classified as cyclic hemiketals. Fructose has two hemiketal isomers; the 5-membered ring called fructofuranose and the 6-membered ring called fructopyranose, the pyranose form being the most stable isomer. Both forms are shown below. Fructose is a commercially available compound. Fructose is very well tolerated and using hyperpolarised $^{13}$C-fructose as an imaging agent is advantageous from a safety perspective.

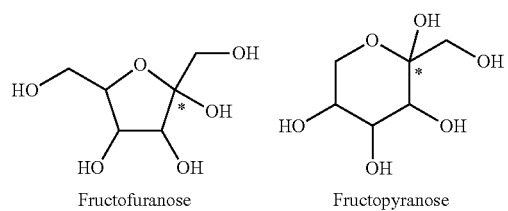 [SMILES: OCC1OC(O)(CO)C(O)C1O ; OCC1(O)OCC(O)C(O)C1O]

Fructofuranose      Fructopyranose

The term "fructose", unless specified otherwise, denotes the D-isomer of fructofuranose or fructopyranose either in the α or β form, and mixtures of these. Hence, the imaging medium according to the invention may thus comprise hyperpolarised $^{13}$C-α-D- or $^{13}$C-β-D-fructopyranose or $^{13}$C-α-D- or $^{13}$C-β-D fructofuranose or a mixture thereof.

The isotopic enrichment of the hyperpolarised $^{13}$C-fructose used in the method of the invention is preferably at least 75%, more preferably at least 80% and especially preferably at least 90%, an isotopic enrichment of over 90% being most preferred. Ideally, the enrichment is 100%. $^{13}$C-fructose used in the imaging medium and the method of the invention is isotopically enriched at the C2-position, i.e. [2-$^{13}$C]-fructose. This is shown in the structures above, wherein * denotes the $^{13}$C-label.

Hence, in one embodiment the imaging medium comprises hyperpolarised [2-$^{13}$C]-fructose.

The terms "hyperpolarised" and "polarised" are used interchangeably hereinafter and denote a nuclear polarisation level in excess of 0.1%, more preferred in excess of 1% and most preferred in excess of 10%.

Due to chemical shift anisotropy, carbonyl carbons tend to decrease in $T_1$, leading to faster polarisation decay with higher field. This behaviour does not hold for the hemiketal of fructose, showing a lengthening of $T_1$ with field strength. Relaxation times of 15-16 seconds, at 11.7 T and 13-14 seconds at 3T have been achieved. The reason is that fructose relaxation is dominated by dipolar relaxation from neighbouring protons. Despite of this, the $C_2$ of fructose, has a long enough relaxation time to provide metabolic information in the time scale of hyperpolarized spectroscopy.

A lengthening of $T_1$ can be obtained by selectively deuterating the C-1 and C-3 directly attached protons to further increase the signal-to-noise ratio or the imaging window.

The level of polarisation may for instance be determined by solid state $^{13}$C-NMR measurements in solid hyperpolarised $^{13}$C-fructose, e.g. solid hyperpolarised $^{13}$C-fructose obtained by dynamic nuclear polarisation (DNP) of $^{13}$C-fructose. The solid state $^{13}$C-NMR measurement preferably consists of a simple pulse-acquire NMR sequence using a low flip angle. The signal intensity of the hyperpolarised $^{13}$C-fructose in the NMR spectrum is compared with signal intensity of $^{13}$C-fructose in a NMR spectrum acquired before the polarisation process. The level of polarisation is then calculated from the ratio of the signal intensities before and after polarisation.

In a similar way, the level of polarisation for dissolved hyperpolarised $^{13}$C-fructose may be determined by liquid state NMR measurements. Again the signal intensity of the dissolved hyperpolarised $^{13}$C-fructose is compared with the signal intensity of the dissolved $^{13}$C-fructose before polarisation (or after the polarization has returned to thermal equilibrium level). The level of polarisation achieved is then calculated from the ratio of the signal intensities of $^{13}$C-fructose before and after polarisation.

Hyperpolarisation of NMR active $^{13}$C-nuclei may be achieved by different methods which are for instance described in WO-A-98/30918, WO-A-99/24080 and WO-A-99/35508, and which all are incorporated herein by reference. Hyperpolarisation methods known in the art are polarisation transfer from a noble gas, "brute force", spin refrigeration, the parahydrogen method and dynamic nuclear polarisation (DNP).

One way for obtaining hyperpolarised $^{13}$C-fructose is the polarisation transfer from a hyperpolarised noble gas which is described in WO-A-98/30918. Noble gases having non-zero nuclear spin can be hyperpolarised by the use of circularly polarised light. A hyperpolarised noble gas, preferably He or Xe, or a mixture of such gases, may be used to effect hyperpolarisation of $^{13}$C-nuclei. The hyperpolarised gas may be in the gas phase, it may be dissolved in a liquid/solvent, or the hyperpolarised gas itself may serve as a solvent. Alternatively, the gas may be condensed onto a cooled solid surface and used in this form, or allowed to sublime. Intimate mixing of the hyperpolarised gas with $^{13}$C-fructose is preferred.

Another way for obtaining hyperpolarised $^{13}$C-fructose is that polarisation is imparted to $^{13}$C-nuclei by thermodynamic equilibration at a very low temperature and high field. Hyperpolarisation compared to the operating field and temperature of the NMR spectrometer is effected by use of a very high field and very low temperature (brute force). The magnetic field strength used should be as high as possible, suitably higher than 1 T, preferably higher than 5 T, more preferably 15 T or more and especially preferably 20 T or more. The temperature should be very low. e.g. 4.2 K or less, preferably 1.5 K or less, more preferably 1.0 K or less, especially preferably 100 mK or less.

Another way for obtaining hyperpolarised $^{13}$C-fructose is the spin refrigeration method. This method covers spin polarisation of a solid compound or system by spin refrigeration polarisation. The system is doped with or intimately mixed with suitable crystalline paramagnetic materials such as $Ni^{2+}$, lanthanide or actinide ions with a symmetry axis of order three or more. The instrumentation is simpler than required for DNP with no need for a uniform magnetic field since no resonance excitation field is applied. The process is carried out by physically rotating the sample around an axis perpendicular to the direction of the magnetic field. The prerequisite for this method is that the paramagnetic species has a highly anisotropic g-factor. As a result of the sample rotation, the electron paramagnetic resonance will be brought in contact with the nuclear spins, leading to a decrease in the nuclear spin temperature. Sample rotation is carried out until the nuclear spin polarisation has reached a new equilibrium.

In a preferred embodiment. DNP (dynamic nuclear polarisation) is used to obtain hyperpolarised $^{13}$C-fructose. In DNP, polarisation of MR active nuclei in a compound to be polarised is affected by a polarisation agent or so-called DNP agent, a compound comprising unpaired electrons. During the DNP process, energy, normally in the form of microwave radiation, is provided, which will initially excite the DNP agent. Upon decay to the ground state, there is a transfer of polarisation from the unpaired electron of the DNP agent to the NMR active nuclei of the compound to be polarised, e.g. to the $^{13}$C nuclei in $^{13}$C-fructose.

To polarise a chemical entity, i.e. compound, by the DNP method, a composition comprising the compound to be polarised and a DNP agent is prepared which is then frozen and inserted into a DNP polariser for polarisation. After the polarisation, the frozen solid hyperpolarised composition is rapidly transferred into the liquid state either by melting it or by dissolving it in a suitable dissolution medium. Dissolution is preferred and the dissolution process of a frozen hyperpolarised composition and suitable devices therefore are described in detail in WO-A-02/37132. The melting process and suitable devices for the melting are for instance described in WO-A-02/36005.

In order to obtain a high polarisation level in the compound to be polarised said compound and the DNP agent need to be in intimate contact during the DNP process. This is not the case if the composition crystallizes upon being frozen or cooled. To avoid crystallization, glass formers may be included in the composition. Factors that affect a possible need of the glass formers is the concentration of fructose in solution, or if another agent is to be co-polarized along with fructose.

For the hyperpolarisation of $^{13}$C-fructose by DNP, a composition is prepared which comprises $^{13}$C-fructose and a DNP agent.

The DNP agent plays a decisive role in the DNP process as its choice has a major impact on the level of polarisation that can be achieved in $^{13}$C-fructose. A variety of DNP agents, in WO-A-99/35508 denoted "OMRI contrast agents", are known. The use of oxygen-based, sulphur-based or carbon-based stable trityl radicals as described in WO-A-99/35508, WO-A-88/10419, WO-A-90/00904, WO-A-91/12024, WO-A-93/02711 or WO-A-96/39367 has resulted in high levels of polarisation in a variety of different samples.

In a preferred embodiment, the hyperpolarised $^{13}$C-fructose used in the method of the invention is obtained by DNP and the DNP agent used is a trityl radical. As briefly mentioned above, the large electron spin polarisation of the DNP agent, i.e. trityl radical is converted to nuclear spin polarisation of $^{13}$C nuclei in $^{13}$C-fructose via microwave irradiation close to the electron Larmor frequency. The microwaves stimulate communication between electron and nuclear spin systems via e-e and e-n transitions. For effective DNP, i.e. to achieve a high level of polarisation in $^{13}$C-fructose, the trityl radical has to be stable and soluble in these compounds to achieve intimate contact between $^{13}$C-fructose and the trityl radical which is necessary for the aforementioned communication between electron and nuclear spin systems.

In a preferred embodiment, the trityl radical is a radical of the formula (1)

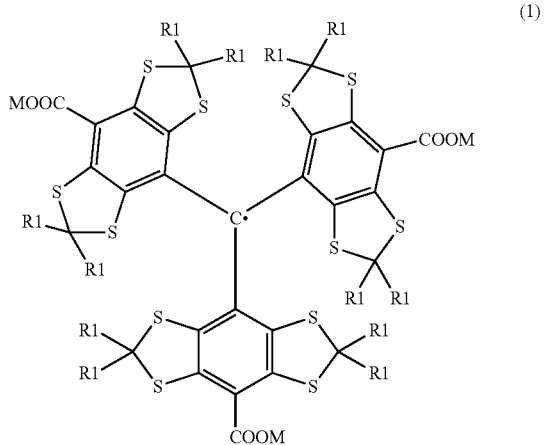

(1)

wherein
M represents hydrogen or one equivalent of a cation; and
R1 which is the same or different represents a straight chain or branched $C_1$-$C_6$-alkyl group optionally substituted by one or more hydroxyl groups or a group —$(CH_2)_n$—X—R2,
 wherein n is 1, 2 or 3;
 X is O or S; and
 R2 is a straight chain or branched $C_1$-$C_4$-alkyl group, optionally substituted by one or more hydroxyl groups.

In a preferred embodiment, M represents hydrogen or one equivalent of a physiologically tolerable cation. The term "physiologically tolerable cation" denotes a cation that is tolerated by the human or non-human animal living body. Preferably, M represents hydrogen or an alkali cation, an ammonium ion or an organic amine ion, for instance meglumine. Most preferably, M represents hydrogen or sodium.

R1 is preferably the same, more preferably a straight chain or branched $C_1$-$C_4$-alkyl group, most preferably methyl, ethyl or isopropyl; or R1 is preferably the same, more preferably a straight chain or branched $C_1$-$C_4$-alkyl group which is substituted by one hydroxyl group, most preferably —$CH_2$—$CH_2$—OH; or R1 is preferably the same and represents —$CH_2$—$OCH_3$—, —$CH_2$—$OC_2H_4OH$, —$CH_2$—$OC_2H_5$, —$CH_2$—$CH_2$—$OCH_3$, —$CH_2$—$SCH_3$, —$CH_2$—$SC_2H_5$ or —$CH_2$—$CH_2$—$SCH_3$, and most preferably —$CH_2$—$CH_2$—$OCH_3$.

In a particularly preferred embodiment, X represents O, M represents an alkali cation, most preferably sodium, and R1 is —$CH_2$—$CH_2$—$OCH_3$.

The aforementioned trityl radical of formula (1) may be synthesized as described in detail in WO-A-88/10419, WO-A-90/00904, WO-A-91/12024, WO-A-93/02711, WO-A-96/39367. WO-A-97/09633, WO-A-98/39277 and WO-A-2006/011811.

For the DNP process, a solution of the starting material $^{13}$C-fructose (in the following denoted "sample") and the DNP agent, preferably a trityl radical, more preferably a trityl radical of formula (1) is prepared. A solvent or a solvent mixture may be used to promote dissolution of the DNP agent in the sample. However, if the hyperpolarised $^{13}$C-fructose is intended to be used as an imaging agent for in vivo $^{13}$C-MR detection, it is preferred to keep the amount of solvent to a minimum or, if possible, to avoid the use of solvents. To be used as an in vivo imaging agent, the polarised $^{13}$C-fructose is usually administered in relatively high concentrations. i.e. a highly concentrated sample is preferably used in the DNP process and hence the amount of solvent is preferably kept to a minimum. In this context, it is also important to mention that the mass of the composition containing the sample, i.e. DNP agent, sample and if necessary solvent, is kept as small as possible. A high mass will have a negative impact on the efficiency of the dissolution process, if dissolution is used to convert the solid composition containing the hyperpolarised $^{13}$C-fructose after the DNP process into the liquid state, e.g. for using it as an imaging agent for $^{13}$C-MR detection. This is due to the fact that for a given volume of dissolution medium in the dissolution process, the mass of the composition to dissolution medium ratio decreases, when the mass of the composition increases. Further, using certain solvents may require their removal before the hyperpolarised $^{13}$C-fructose used as an MR imaging agent is administered to a human or non-human animal being since they might not be physiologically tolerable.

Using $^{13}$C-fructose as a starting material to obtain hyperpolarised $^{13}$C-fructose via DNP, a solvent is normally added to prepare a solution of the DNP agent and the $^{13}$C-fructose. Preferably an aqueous carrier and most preferably water is used as a solvent. In one embodiment, the DNP agent is dissolved and the $^{13}$C-fructose is subsequently dissolved in the dissolved DNP agent. In another embodiment, $^{13}$C-fructose is dissolved in the solvent and subsequently the DNP agent is dissolved in the dissolved $^{13}$C-fructose. Intimate mixing of the compounds can be promoted by several means known in the art, such as stirring, vortexing or sonication.

If the hyperpolarised $^{13}$C-fructose used in the method of the invention is obtained by DNP, the composition to be polarised comprising $^{13}$C-fructose and a DNP agent may further comprise a paramagnetic metal ion. It has been found that the presence of paramagnetic metal ions may result in increased polarisation levels in the compound to be polarised by DNP as described in detail in WO-A2-2007/064226 which is incorporated herein by reference. The term "paramagnetic metal ion" denotes paramagnetic metal ions in the form of their salts and paramagnetic chelates, i.e. chemical entities comprising a chelator and a paramagnetic metal ion, wherein said paramagnetic metal ion and said chelator form a complex.

In a preferred embodiment, the paramagnetic metal ion is a compound comprising $Gd^{3+}$ as a paramagnetic metal ion, preferably a paramagnetic chelate comprising a chelator and $Gd^{3+}$ as a paramagnetic metal ion. In a more preferred embodiment, said paramagnetic metal ion is soluble and stable in the composition to be polarised.

As with the DNP agent described before, the $^{13}C$-fructose to be polarised must be in intimate contact with the paramagnetic metal ion as well. The composition used for DNP comprising $^{13}C$-fructose, a DNP agent and a paramagnetic metal ion may be obtained in several ways. In a first embodiment the $^{13}C$-fructose is dissolved in a suitable solvent to obtain a solution. To this solution of $^{13}C$-fructose the DNP agent is added and dissolved. The DNP agent, preferably a trityl radical, might be added as a solid or in solution, preferably as a solid. In a subsequent step, the paramagnetic metal ion is added. The paramagnetic metal ion might be added as a solid or in solution, preferably as a solid. In another embodiment, the DNP agent and the paramagnetic metal ion are dissolved in a suitable solvent and this solution is added to $^{13}C$-fructose. In yet another embodiment, the DNP agent (or the paramagnetic metal ion) is dissolved in a suitable solvent and added to $^{13}C$-fructose. In a subsequent step the paramagnetic metal ion (or the DNP agent) is added to this solution, either as a solid or in solution, preferably as a solid. Preferably, the amount of solvent to dissolve the paramagnetic metal ion (or the DNP agent) is kept to a minimum. Again intimate mixing of the compounds can be promoted by several means known in the art, such as stirring, vortexing or sonication.

If a trityl radical is used as DNP agent, a suitable concentration of such a trityl radical in the composition is 1 to 25 mM, preferably 2 to 20 mM, more preferably 10 to 15 mM in the composition used for DNP. If a paramagnetic metal ion is added to the composition, a suitable concentration of such a paramagnetic metal ion is 0.1 to 6 mM (metal ion) in the composition, and a concentration of 0.5 to 4 mM is preferred.

After having prepared a composition comprising $^{13}C$-fructose, the DNP agent and optionally a paramagnetic metal ion, said composition is frozen by methods known in the art, e.g. by freezing it in a freezer, in liquid nitrogen or by simply placing it in the DNP polariser, where liquid helium will freeze it. The composition may optionally be frozen as "beads" before it is inserted into the polariser. Such beads may be obtained by adding the composition drop wise to liquid nitrogen. A more efficient dissolution of such beads has been observed, which is especially relevant if larger amounts of $^{13}C$-fructose are polarised, for instance when it is intended to use the polarised $^{13}C$-fructose in an in vivo $^{13}C$-MR detection method.

If a paramagnetic metal ion is present in the composition said composition may be degassed before freezing, e.g. by bubbling helium gas through the composition (for instance for a time period of 2-15 min) but degassing can be effected by other known common methods.

The DNP technique is for instance described in WO-A-98/58272 and in WO-A-01/96895, both of which are included by reference herein. Generally, a moderate or high magnetic field and a very low temperature are used in the DNP process, e.g. by carrying out the DNP process in liquid helium and a magnetic field of about 1 T or above. Alternatively, a moderate magnetic field and any temperature at which sufficient polarisation enhancement is achieved may be employed. In a preferred embodiment, the DNP process is carried out in liquid helium and a magnetic field of about 1 T or above.

Suitable polarisation units are for instance described in WO-A-02/37132. In a preferred embodiment, the polarisation unit comprises a cryostat and polarising means, e.g. a microwave chamber connected by a wave guide to a microwave source in a central bore surrounded by magnetic field producing means such as a superconducting magnet. The bore extends vertically down to at least the level of a region P near the superconducting magnet where the magnetic field strength is sufficiently high, e.g. between 1 and 25 T, for polarisation of the sample nuclei to take place. The bore for the probe (i.e. the frozen composition to be polarised) is preferably sealable and can be evacuated to low pressures, e.g. pressures in the order of 1 mbar or less. A probe introducing means such as a removable transporting tube can be contained inside the bore and this tube can be inserted from the top of the bore down to a position inside the microwave chamber in region P. Region P is cooled by liquid helium to a temperature low enough to for polarisation to take place, preferably temperatures of the order of 0.1 to 100 K, more preferably 0.5 to 10 K, most preferably 1 to 5 K. The probe introducing means is preferably sealable at its upper end in any suitable way to retain the partial vacuum in the bore. A probe-retaining container, such as a probe-retaining cup, can be removably fitted inside the lower end of the probe introducing means. The probe-retaining container is preferably made of a light-weight material with a low specific heat capacity and good cryogenic properties such as e.g. KelF (polychlorotrifluoro-ethylene) or PEEK (polyetheretherketone) and it may be designed in such a way that it can hold more than one probe.

The probe is inserted into the probe-retaining container, submerged in the liquid helium and irradiated with microwaves. The microwave frequency may be determined from the EPR line of the DNP agent, which depends on the magnetic field of the magnet as 28.0 GHz/T. The optimal microwave frequency may be determined by adjusting the frequency for maximal NMR signal. Preferably, the optimal microwave frequency is in the about 94 GHz for a magnet charged to 3.35 T, 110 GHz for a magnet charged to 4 T, 140 GHz for a magnet charged to 5 T and 200 GHz for a magnet charged to 7 T. The power may be chosen between 50 and 200 mW, dependent on the probe size. The level of polarisation may be monitored as earlier described by for instance acquiring solid state $^{13}C$-NMR signals of the probe during microwave irradiation. Generally, a saturation curve is obtained in a graph showing NMR signal vs. time. Hence it is possible to determine when the optimal polarisation level is reached. A solid state $^{13}C$-NMR measurement suitably consists of a simple pulse-acquire NMR sequence using a low flip angle. The signal intensity of the dynamic nuclear polarised nuclei, i.e. $^{13}C$ nuclei in $^{13}C$-fructose is compared with the signal intensity of the $^{13}C$. nuclei in $^{13}C$-fructose before DNP. The polarisation is then calculated from the ratio of the signal intensities before and after DNP.

After the DNP process, the frozen solid composition comprising the hyperpolarised $^{13}C$-fructose is transferred from the solid state to the liquid state, i.e. liquefied. This can be done by dissolution in an appropriate solvent or solvent mixture (dissolution medium) or by melting the solid composition, e.g. by applying energy in the form of heat. Dissolution is preferred and the dissolution process and suitable devices therefore are described in detail in WO-A-02/37132. The melting process and suitable devices for the melting are for instance described in WO-A-02/36005. Briefly, a dissolution unit/melting unit is used which is either physically separated from the polariser or is a part of an apparatus that contains the polariser and the dissolution unit/melting unit. In a preferred embodiment, dissolution/melting is carried out at an elevated magnetic field, e.g. inside the polariser, to improve the relaxation and retain a maximum of the hyperpolarisation. Field nodes should be avoided and low field may lead to enhanced relaxation despite the above measures.

If the composition comprising the hyperpolarised $^{13}$C-fructose is liquefied by dissolution, an aqueous carrier, preferably a physiologically tolerable and pharmaceutically accepted aqueous carrier like water, a buffer solution or saline is suitably used as a solvent especially preferably if the hyperpolarised $^{13}$C-fructose is intended for use in an imaging medium for in vivo $^{13}$C-MR detection. For in vitro applications also non aqueous solvents or solvent mixtures may be used, for instance DMSO or methanol or mixtures comprising an aqueous carrier and a non aqueous solvent, for instance mixtures of DMSO and water or methanol and water.

The terms "buffer solution" and "buffer" are hereinafter used interchangeably. In the context of this application "buffer" denotes one or more buffers, i.e. also mixtures of buffers.

Preferred buffers are physiologically tolerable buffers, more preferably buffers which buffer in the range of about pH 7 to 8 like for instance phosphate buffer ($KH_2PO_4$/$Na_2HPO_4$), ACES, PIPES, imidazole/HCl, BES, MOPS, HEPES, TES, TRIS, HEPPS or TRICIN.

In another preferred embodiment, the aqueous carrier or, where applicable,—the combined aqueous carrier/base solution further comprises one or more compounds which are able to bind or complex free paramagnetic ions, e.g. chelating agents like DTPA or EDTA.

If hyperpolarisation is carried out by the DNP method, the DNP agent, preferably a trityl radical and the optional paramagnetic metal ion may be removed from the liquid containing the hyperpolarised $^{13}$C-fructose. Removal of these compounds is preferred if the hyperpolarised $^{13}$C-fructose is intended for use in an imaging medium for in vivo use.

Methods useful to remove the trityl radical and the paramagnetic metal ion are known in the art and described in detail in WO-A2-2007/064226 and WO-A1-2006/011809, which are incorporated herein by reference.

In a preferred embodiment the hyperpolarised $^{13}$C-fructose used in the method of the invention is obtained by dynamic nuclear polarisation of a composition that comprises $^{13}$C-fructose, a trityl radical of formula (1) and optionally a paramagnetic chelate comprising $Gd^{3+}$. In this preferred embodiment, a solution of the trityl radical and, if used, the paramagnetic chelate comprising $Gd^{3+}$ is prepared. The dissolved trityl radical and the optional dissolved paramagnetic chelate are added to sodium $^{13}$C-fructose and the composition is preferably sonicated or whirl-mixed to promote intimate mixing of all the components.

The imaging medium according to the method of the invention may be used as imaging medium for in vitro $^{13}$C-MR detection, e.g. $^{13}$C-MR detection in cell cultures, body samples, ex vivo tissue or isolated organs derived from the human or non-human animal body. For this purpose, the imaging medium is provided as a composition that is suitable for being added to, for instance, cell cultures, samples like urine, blood or saliva, ex vivo tissues like biopsy tissues or isolated organs. Such an imaging medium preferably comprises in addition to the imaging agent, i.e. the MR active agent hyperpolarised $^{13}$C-fructose, a solvent which is compatible with and used for in vitro cell or tissue assays, for instance DMSO or methanol or solvent mixtures comprising an aqueous carrier and a non aqueous solvent, for instance mixtures of DMSO and water or a buffer solution or methanol and water or a buffer solution. As it is apparent for the skilled person, pharmaceutically acceptable carriers, excipients and formulation aids may be present in such an imaging medium but are not required for such a purpose.

Further, the imaging medium according to the method of the invention may be used as imaging medium for in vivo $^{13}$C-MR detection, i.e. $^{13}$C-MR detection carried out on living human or non-human animal beings. For this purpose, the imaging medium needs to be suitable for administration to a living human or non-human animal body. Hence such an imaging medium preferably comprises in addition to the imaging agent, i.e. the MR active agent hyperpolarised $^{13}$C-fructose, an aqueous carrier, preferably a physiologically tolerable and pharmaceutically accepted aqueous carrier like water, a buffer solution or saline. Such an imaging medium may further comprise conventional pharmaceutical or veterinary carriers or excipients, e.g. formulation aids such as stabilizers, osmolality adjusting agents, solubilising agents and the like which are conventional for diagnostic compositions in human or veterinary medicine.

If the imaging medium used in the method of the invention is used for in vivo $^{13}$C-MR detection, i.e. in a living human or non-human animal body, said imaging medium is preferably administered to said body parenterally, preferably intravenously. Generally, the body under examination is positioned in an MR magnet. Dedicated $^{13}$C-MR RF-coils are positioned to cover the area of interest. Dosage and concentration of the imaging medium will depend upon a range of factors such as toxicity and the administration route. At less than 400 s after the administration, preferably less than 120 s, more preferably less than 60 s after the administration, especially preferably 20 to 50 s an MR imaging sequence is applied that encodes the volume of interest in a combined frequency and spatial selective way. The exact time of applying an MR sequence is highly dependent on the volume of interest and on the species.

In the $^{13}$C-MR detection method according to the invention, it is preferred to detect signals of $^{13}$C-fructose, including all isomers. $^{13}$C-fructose-6-phosphate and $^{13}$C-fructose-1-phosphate. The one-step metabolism via hexokinase to fructose-6-phosphate is analogous to the first step of glycolysis. The reaction of hyperpolarised fructose with hexokinase yields the phosphorylated pentose, i.e. fructofuranose-6-phosphate, within seconds. Hence, detection of $^{13}$C-fructose-6-phosphate includes detection of $^{13}$C-fructofuranose-6-phosphate. Fructose can also be metabolized to the fructose-1-phosphate via fructokinase, a reaction that takes place primarily in the liver. Using hyperpolarised $^{13}$C-fructose as an imaging agent cancer can be discriminated from normal tissue based on the detection of hyperpolarized fructofuranose-6-phosphate. The enzymatic conversion of hyperpolarized fructose allows the probing of important changes in glycolytic metabolism upstream of pyruvate, including upregulated hexose uptake, hexokinase activity and changes in flux through the pentose phosphate pathway.

Thus in a preferred embodiment it is provided a method of $^{13}$C-MR detection using an imaging medium comprising hyperpolarised $^{13}$C-fructose, wherein signals of $^{13}$C-fructose, $^{13}$C-fructose-6-phosphate and $^{13}$C-fructose-1-phosphate, preferably signals of $^{13}$C-fructose and $^{13}$C-fructofuranse-6-phosphate are detected.

The term "signal" in the context of the invention refers to the MR signal amplitude or integral or peak area to noise of peaks in a $^{13}$C-MR spectrum which represent $^{13}$C-fructose, or its metabolites. In a preferred embodiment, the signal is the peak area.

In a preferred embodiment of the method of the invention, the above-mentioned signals of $^{13}$C-fructose and its metabolites are used to generate a metabolic profile.

In one embodiment, the above-mentioned signals of $^{13}$C-fructose and its metabolites are used to generate a metabolic profile of a living human or non-human animal being. Said metabolic profile may be derived from the whole body, e.g. obtained by whole body in vivo $^{13}$C-MR detection. Alternatively, said metabolic profile is generated from a region of interest, i.e. a certain tissue, organ or part of said human or non-human animal body. Particularly, said metabolic profile may be derived from a region affected by cancer as metabolism of fructose is implicated in the pathogenesis of specific types of cancer, such as e.g. breast cancer and prostate cancer.

In another embodiment, the above-mentioned signals of $^{13}$C-fructose and its metabolites are used to generate a metabolic profile of cells in a cell culture, of samples like urine, blood or saliva, of ex vivo tissue like biopsy tissue or of an isolated organ. Said metabolic profile is then generated by in vitro $^{13}$C-MR detection.

Thus in a preferred embodiment it is provided a method of $^{13}$C-MR detection using an imaging medium comprising hyperpolarised $^{13}$C-fructose, wherein signals of $^{13}$C-fructose and its metabolites are detected and wherein said signals are used to generate a metabolic profile.

In one embodiment, the spectral signal intensities of $^{13}$C-fructose and its metabolites ($^{13}$C-labelled compounds) are used to generate the metabolic profile. In another embodiment, the spectral signal integrals of the $^{13}$C-labelled compounds are used to generate the metabolic profile. In another embodiment, signal intensities from separate images of the $^{13}$C-labelled compounds are used to generate the metabolic profile. In yet another embodiment, the signal intensities of the $^{13}$C-labelled compounds are obtained at two or more time points to calculate the rate of change of the $^{13}$C-labelled compounds.

In another embodiment the metabolic profile includes or is generated using processed signal data of the $^{13}$C-labelled compounds, e.g. ratios of signals, corrected signals, or dynamic or metabolic rate constant information deduced from the signal pattern of multiple MR detections, i.e. spectra or images. Thus, in a preferred embodiment a corrected $^{13}$C-fructose signal, i.e. $^{13}$C-fructose to $^{13}$C-fructose-6-phosphate signal and/or $^{13}$C-fructose to $^{13}$C-fructose-1-phosphate signal is included into or used to generate the metabolic profile. In a further preferred embodiment, a corrected $^{13}$C-fructose to total $^{13}$C-carbon signal is included into or used to generate the metabolic profile with the total $^{13}$C-carbon signal being the sum of the signals of $^{13}$C-labelled compounds.

The metabolic profile generated in the preferred embodiment of the method according to the invention provides information about the metabolic status and activity of the body, part of the body, cells, tissue, body sample etc under examination and said information may be used in a subsequent step for, e.g. identifying diseases, monitoring the course of a disease and/or determining a disease state or for monitoring therapy.

Such a disease may be a tumour since tumour tissue is usually characterized by a higher metabolic activity than healthy tissue. Such a higher metabolic activity can be determined by comparing the metabolic profile of a tumour or of an ex vivo sample of a tumour with the metabolic profile of healthy tissue (e.g. surrounding tissue or healthy ex vivo tissue) and may manifest itself in said metabolic profile by high signals of the $^{13}$C-labelled compounds or high corrected $^{13}$C-fructose signal or high metabolic rates, or high fructose-6-phosphate signal, or high fructose-6-phosphate to fructose ratio.

Another disease may be ischemia in the heart since ischemic myocardial tissue is usually characterized by a lower metabolic activity than healthy myocardial tissue. Again such a lower metabolic activity can be determined by comparing the metabolic profile of ischemic myocardial tissue with the metabolic profile of healthy myocardial tissue. Further, as $^{13}$C-fructose will likely cross the blood-brain barrier at a greater rate than other known agents it may also be useful for neuro applications.

Yet another disease may be liver related diseases, such as non-alcoholic fatty liver disease.

Another aspect of the invention is a composition comprising sodium $^{13}$C-fructose, a trityl radical and optionally a paramagnetic metal ion.

In a first embodiment, said composition comprises $^{13}$C-fructose, a trityl radical and optionally a paramagnetic metal ion. In a preferred embodiment, said $^{13}$C-fructose is [2-$^{13}$C]-fructose. In another preferred embodiment, said trityl radical is a trityl radical of formula (1) wherein M represents hydrogen or sodium and R1 is preferably the same, more preferably a straight chain or branched $C_1$-$C_4$-alkyl group, most preferably methyl, ethyl or isopropyl; or R1 is preferably the same, more preferably a straight chain or branched $C_1$-$C_4$-alkyl group which is substituted by one hydroxyl group, most preferably —$CH_2$—$CH_2$—OH; or R1 is preferably the same and represents —$CH_2$—$CH_2$—O—$CH_3$.

In another preferred embodiment said composition comprises a paramagnetic metal ion, and said paramagnetic metal ion is preferably a compound comprising $Gd^{3+}$ as a paramagnetic metal ion, preferably a paramagnetic chelate comprising a chelator and $Gd^{3+}$ as a paramagnetic metal ion. Suitably, said composition further comprises a solvent or solvents: preferably an aqueous carrier and most preferably water is used as a solvent. The aforementioned compositions can be used for obtaining hyperpolarised sodium $^{13}$C-fructose by dynamic nuclear polarisation (DNP) with a high polarisation level.

The invention is illustrated by the following non-limiting examples:

EXAMPLES

Example 1

Hyperpolarization of Fructose

A 4.0M solution of 2-[$^{13}$C]-fructose (Isotec, Miamisburg, Ohio) in water containing 15 mM OX063 trityl radical (Oxford Instruments) was hyperpolarized on a Hypersense instrument (Oxford Instruments) as described by Ardenkjaer-Larsen et al (2003) Increase in signal-to-noise ratio of >10,000 times in liquid-state NMR. *Proc. Natl. Acad. Sci. U.S.A.* 100, 10158-10163. The frozen sample was dissolved in 1× phosphate buffered saline (PBS), with a resultant pH of 7.6, and transferred immediately to a 10 mm NMR tube.

Figure 2:
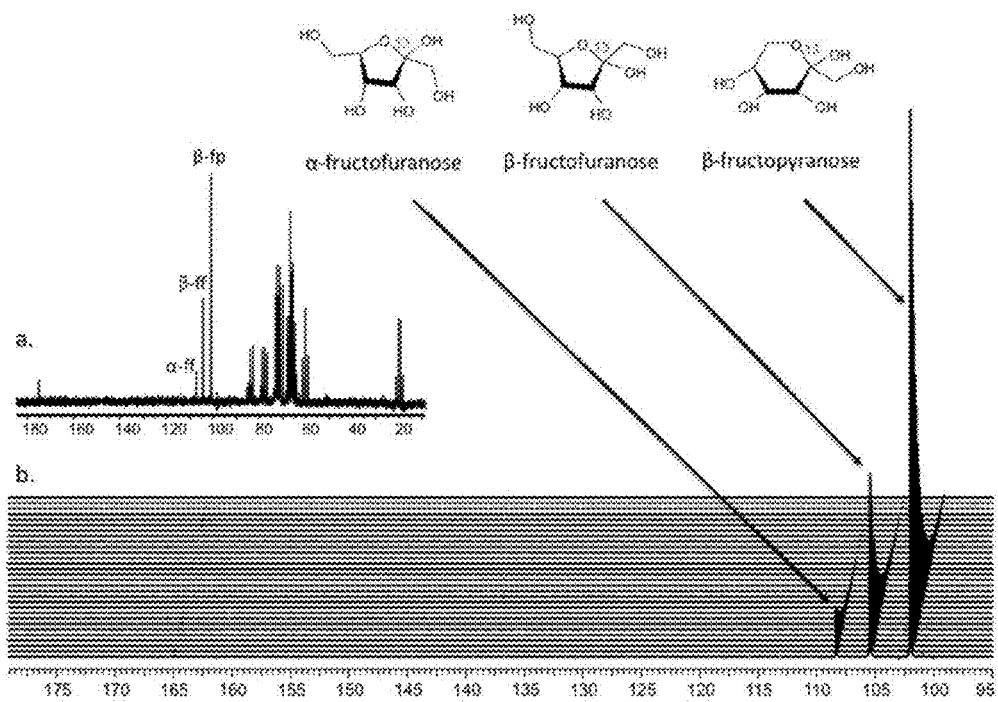
FIG. 2. The natural abundance spectrum of fructose (a) and DNP spectrum of [2-$^{13}$C]-fructose (b). The linear form is present in the DNP spectrum, but at a very low level analogous to the thermal spectrum. (Top) Structures of each of the isomers are shown with their analogous resonance.

11.7T NMR Studies:

NMR studies were performed on an 11.7T Varian INOVA spectrometer (125 MHz $^{13}$C, Varian Instruments) using a 10 mm $^{15}$N/$^{51}$P/$^{13}$C triple-tuned direct detect probe. Initially, a thermal spectrum was acquired for a natural abundance fructose sample in 1×PBS buffer at 37° C. (nt=9000, sw=30000, np=30000, TR=3.5 s, acq time=0.5 s) using an Ernst angle pulse (45 degrees). FIG. 2 demonstrates the natural abundance $^{13}$C spectrum of fructose. The $C_2$ carbon resonances correspond to the isomeric distribution of the two ring forms (pyranose and furanose forms) of the fructose molecule.

For the acquisition of hyperpolarized $^{13}$C spectra eighty pulse hyperpolarized $^{13}$C NMR spectra (1 average, spectral window=30000 Hz, number of points=30000, TR=3.5 s, acq time=0.5 s, total acq time=2 min 55 s) were acquired using a 5° pulse and proton decoupled using a waltz-16 decoupling scheme. Hyperpolarized studies were followed by acquisition of thermal data using nearly identical parameters, using a 90° tip angle and a repeat time of roughly four $T_1$'s (TR=76 s, nt=64). $T_1$'s were determined by performing a mono-exponential fit to the signal decay curve of the hyperpolarized compounds. Signal enhancement percent polarizations were calculated by comparing the hyperpolarized and thermal data sets and accounting for differences in tip angle and transients obtained. Solid state polarizations were calculated by correcting the enhancement for the transfer time from the polarizer using the $T_1$ decay.

Example 2

NMR Studies of Metabolism Using [2-$^{13}$C]-Fructose

For NMR studies of the enzymatic conversion of Fructose to fructose-6-phosphate, hyperpolarized [2-$^{13}$C]-fructose was reacted with 400 U of hexokinase (Sigma Aldrich) in the presence of 15 mM ATP, 50 mM TRIS and 13 mM MgCl$_2$. The labelling and mechanism for transport and metabolism is shown below (FIG. 1), though in this enzymatic study the transport element has been removed and the enzyme activity was independently measured. Peaks corresponding to fructose-6-phosphate were identified using a natural abundance carbon spectrum, using a similar set of experimental parameters.

3T Studies:

$T_1$ studies were performed using a 3T GE Signa™ scanner (GE Healthcare. Waukesha, Wis.) equipped with the MNS (multinuclear spectroscopy) hardware package. Solution spectra were acquired using a 5° non localised pulse, TR=3 s and fit to a monoexponential. The RF coil used in these experiments was a dual-tuned $^1$H-$^{13}$C coil with a quadrature $^{13}$C channel and linear $^1$H channel construction based on an earlier design and also used in $^{13}$C-pyruvate mouse imaging studies. For animal studies, $T_2$-weighted fast spin echo images were acquired prior to MRSI studies to denote anatomy and place voxels on the region of interest. In vivo MRSI studies were carried out using a compressed sensing double spin 3D MRSI acquisition scheme as previously published by Hu S et al. (2008) Compressed sensing for resolution enhancement of hyperpolarized 13C flyback 3D-MRSI. *J Magn Reson* 192, 258-264, with a TE=140 ms. TR=215 ms, FOV=8 cm×8 cm, and 16×8 resolution. 500 µl of 80 mM [2-$^{13}$C]-fructose was injected similar to described by Albers M J et al. (2008) Hyperpolarized 13C lactate, pyruvate and alanine: noninvasice biomarkers for prostate cancer detection and grading. *Cancer Res.* 68, 8607-8615, for [1-$^{13}$C] pyruvate in a transgenic model of prostate cancer (TRAMP). These injections were compared to the standard [1-$^{13}$C]-pyruvate injection for the same voxel in a tumor region of interest.

Results:

Calculated $T_1$'s for the $C_2$ fructose carbon are tabulated in Table 1 at both 11.7T and 3T. There is a slight decrease in $T_1$ relaxation of the carbon of interest with decreasing field strength. There was no significant difference in $T_1$ between the isomers of fructose. Percent polarizations show similar values for the isomers of fructose with averages on the order of 12%. There was no $T_1$ dependence on pH observed for pH ranges 5.9-7.8 for fructose.

TABLE 1

$T_1$ relaxation times at 11.7T and 3T and percent polarization for each fructose isomer

| Isomer | $T_1$ sec (11.7T) | $T_1$ sec (3T) | % pol (corrected) |
|---|---|---|---|
| β-fructopyranose | 16.3 ± 0.5 | 14.5 ± 0.3 | 12.0 ± 2.2 |
| β-fructofuranose | 15.8 ± 0.5 | 13.4 ± 2.5 | 11.6 ± 2.5 |
| A-fructofuranose | 15.5 ± 0.5 | 13.4 ± 0.4 | 11.8 ± 2.0 |

Figure 3:
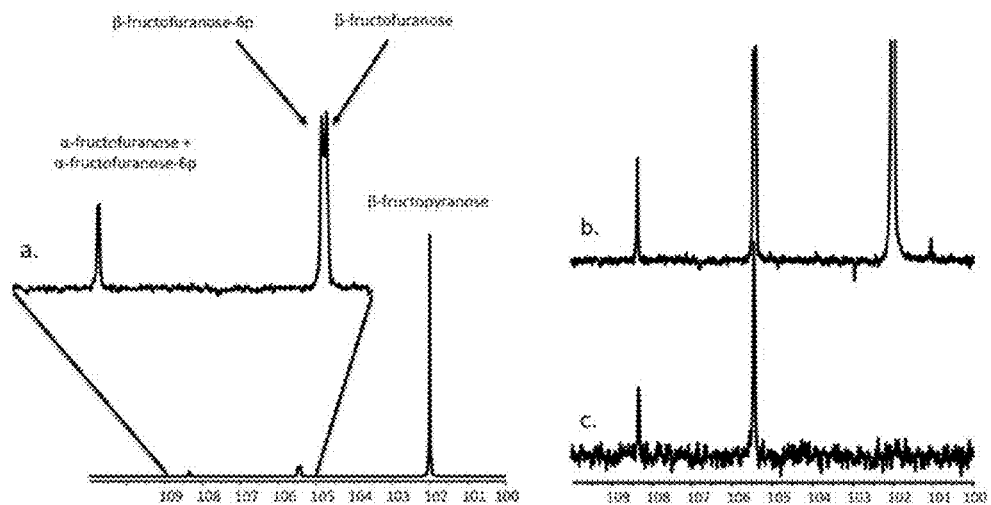
FIG. 3. (a) Spectrum of fructose reacted with 400 U of hexokinase, the zoomed in region demonstrates the resonances corresponding to the fructose and fructose-6-phosphate. (b) The dynamic spectrum after 5 secs of reaction with hexokinase. (c) The thermal spectrum of same solution with hexokinase averaged 85 min post DNP.

The reaction of hyperpolarized $C_2$-fructose with hexokinase yields the phosphorylated pentose within seconds. FIG. 3 demonstrates the conversion within 5 seconds after addition of fructose to the hexokinase in buffer. An expansion of the downfield region of the spectrum (FIG. 3a) shows the split in the 105.5 ppm resonance, which is a combination of both the β-fructo-furanose and the β-fructo-pyranose-6-phosphate. FIG. 3 also compares the first scan of the hyperpolarized acquisition (FIG. 3b) versus the thermal spectrum acquired over 85 minutes post DNP (FIG. 3c). It is apparent that the enzyme has now fully converted the fructose to fructose-6-phosphate and there is no longer a resonance corresponding to β-fructo-pyranose.

Figure 4:
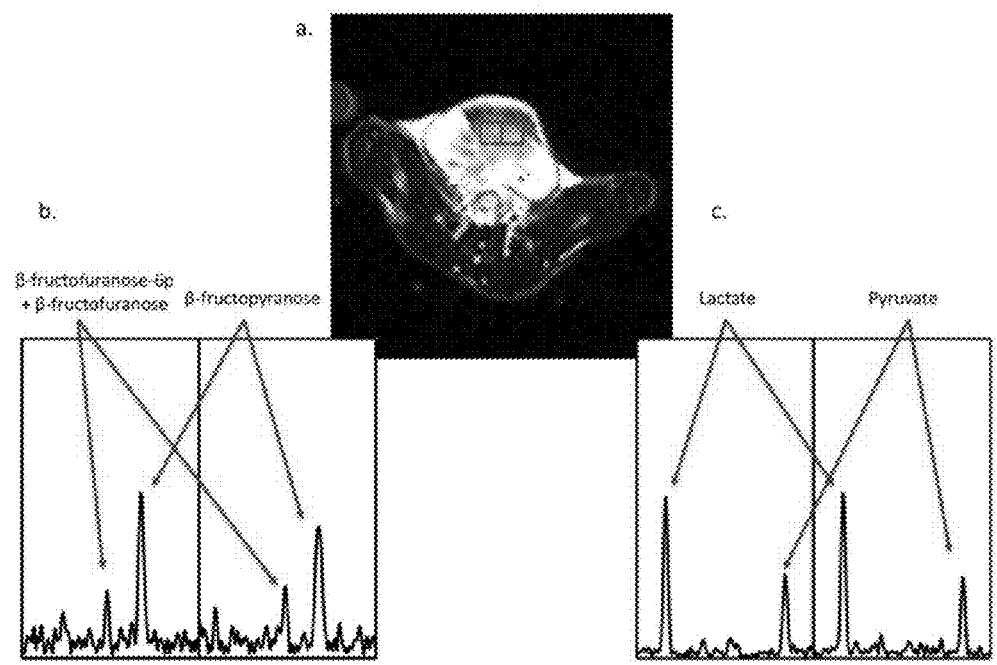
FIG. 4. (a) $T_2$ weighted image of a moderately-late stage TRAMP mouse prostate tumor. (b) Resonances corresponding to fructose and β-fructopyranose and composite β-fructofuranose-6-phosphate and β-fructofuranose are shown as a result of metabolism from the fructose injection. (c) Pyruvate and lactate resonances from the same locations obtained after of hyperpolarized pyruvate in the same mouse.
Figure 5:
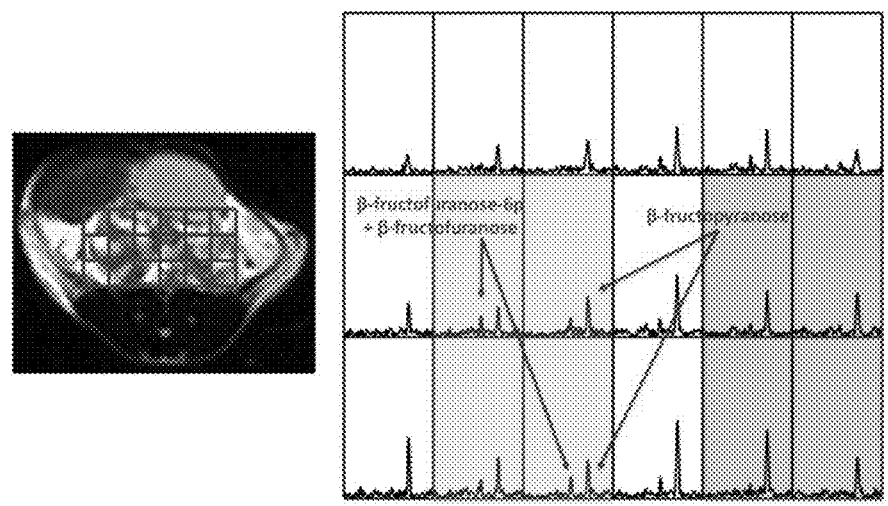
FIG. 5. $^{13}$C spectroscopic image of a TRAMP mouse, showing differential uptake and metabolism of fructose within tumor as compared to surrounding benign tissues. Resonances corresponding to the β-fructopyranose and composite β-fructofuranose-6-phosphate and β-fructofuranose are shown. The light grey area demonstrates a region of diffuse tumor, compared to the benign dark grey area (another lobe of the mouse prostate).

FIG. 4 demonstrates the metabolism following separate injections of 80 mM hyperpolarized fructose (FIG. 4b) and pyruvate (FIG. 4c) in the same TRAMP mouse. The primary TRAMP tumor demonstrates high levels of hyperpolarized lactate, as well good signal to noise spectra of hyperpolarized spectra of fructose and its metabolite β-fructo-furanose-6-phosphate. Because the isomeric ratio of the fructose pyranose to furanose in solution is approximately 77/23, the in vivo peak at 105.5 ppm (and if visible the downstream 108.25 ppm resonance) is mainly due to fructo-furanose-6-phosphate. In this early-to-moderate stage TRAMP tumor, both high levels of LDH activity and possible hexokinase activity were visualized 15 secs post-injection in the same 0.035 cc voxels. This was then taken further and applied to a more diffuse prostate tumor (FIG. 5). The MRSI data demonstrated that the resonance corresponding to the composite β-fructo-furanose and β-fructo-furanose-6-phosphate were higher in the regions of diffuse tumor as compared to surrounding benign tissues. In turn the ratio of this resonance to the β-fructopyranose resonance is increased relative to the surrounding tissue.

What is claimed is:

1. A method of identifying cancer by $^{13}$C-MR detection using an imaging medium comprising hyperpolarised $^{13}$C-fructose, wherein signals of $^{13}$C-fructose, $^{13}$C-fructose-6-phosphate and/or $^{13}$C-fructose-1-phosphate are detected, wherein said hyperpolarized $^{13}$C-fructose is obtained by dynamic nuclear polarisation and wherein the signals of $^{13}$C-fructose and of $^{13}$C-fructose-6-phosphate and/or of $^{13}$C-fructose and of $^{13}$C-fructose-6-phosphate are compared.

2. The method according to claim 1, wherein said signals are used to generate a metabolic profile and wherein said method is a method of in vivo $^{13}$C-MR detection and said metabolic profile is a metabolic profile of a living human or non-human animal being.

3. The method according to claim 1, wherein said signals are used to generate a metabolic profile and wherein said method is a method of in vitro $^{13}$C-MR detection and said metabolic profile is a metabolic profile of cells in a cell culture, of body samples, of ex vivo tissue or of an isolated organ.

4. A composition comprising $^{13}$C-fructose, a trityl radical and a paramagnetic metal ion.

5. The composition according to claim 4, wherein said $^{13}$C-fructose is [2-$^{13}$C]-fructose.

6. The composition according to claim 4, wherein said paramagnetic metal ion is present and is a paramagnetic chelate comprising $Gd^{3+}$.

7. The composition according to claim 4, wherein said trityl radical is a trityl radical of formula (1)

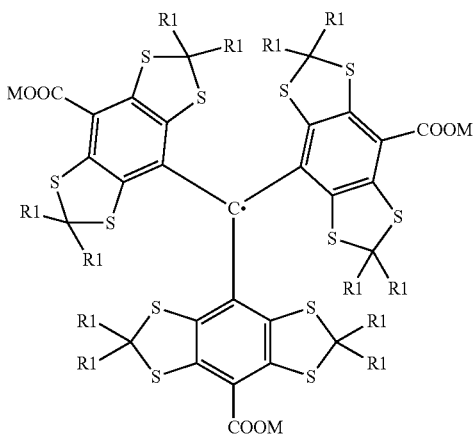

(1)

wherein

M represents hydrogen or one equivalent of a cation; and

R1 which is the same or different represents a straight chain or branched $C_1$-$C_6$-alkyl group optionally substituted by one or more hydroxyl groups or a group —$(CH_2)_n$—X—R2, wherein n is 1, 2 or 3;

X is O or S; and

R2 is a straight chain or branched $C_1$-$C_4$-alkyl group, optionally substituted by one or more hydroxyl groups.

8. The method according to claim 1, wherein signals of $^{13}$C-fructose, and $^{13}$C-fructose-6-phosphate are detected and wherein the signals of $^{13}$C-fructose and of $^{13}$C-fructose-6-phosphate are compared.

9. A method of identifying cancer by $^{13}$C-MR detection using an imaging medium comprising hyperpolarised $^{13}$C-fructose, wherein signals of $^{13}$C-fructose, and $^{13}$C-fructo-furanose-6-phosphate are detected and the ratio of $^{13}$C-fructo-furanose-6-phosphate to $^{13}$C-fructose calculated.

10. The composition according to claim 4, wherein said composition is used for in-vitro $^{13}$C-NMR detection wherein the signals of $^{13}$C-fructose and of $^{13}$C-fructose-6-phosphate and/or of $^{13}$C-fructose and of $^{13}$C-fructose-6-phosphate are compared.

11. The composition according to claim 4, wherein said composition is used to produce hyperpolarized $^{13}$C-fructose for use in a method according to claim 1.

* * * * *